United States Patent
Babaev

(10) Patent No.: US 7,662,177 B2
(45) Date of Patent: Feb. 16, 2010

(54) APPARATUS AND METHODS FOR PAIN RELIEF USING ULTRASOUND WAVES IN COMBINATION WITH CRYOGENIC ENERGY

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 749 days.

(21) Appl. No.: 11/403,283

(22) Filed: Apr. 12, 2006

(65) Prior Publication Data
US 2007/0244528 A1   Oct. 18, 2007

(51) Int. Cl.
*A61N 7/00* (2006.01)
(52) U.S. Cl. ............................. 607/96; 607/50; 607/104
(58) Field of Classification Search ................... 607/50, 607/96, 104
See application file for complete search history.

(56) References Cited

U.S. PATENT DOCUMENTS

| | | | |
|---|---|---|---|
| 4,528,979 A | 7/1985 | Marchenko |
| 4,532,938 A | 8/1985 | Carlisle |
| 4,763,671 A | 8/1988 | Goffinet |
| 4,832,022 A | 5/1989 | Tjulkov et al. |
| 5,115,805 A | 5/1992 | Bommannan et al. |
| 5,186,181 A | 2/1993 | Franconi et al. |
| 5,231,975 A | 8/1993 | Bommannan et al. |
| 5,323,769 A | 6/1994 | Bommannan et al. |
| 5,334,181 A | 8/1994 | Rubinsky et al. |
| 5,413,550 A | 5/1995 | Castel |
| 5,433,739 A | 7/1995 | Sluijter et al. |
| 5,441,490 A | 8/1995 | Svedman |
| 5,445,611 A | 8/1995 | Eppstein et al. |
| 5,460,595 A | 10/1995 | Hall et al. |
| 5,495,039 A | 2/1996 | Frater et al. |
| 5,571,147 A | 11/1996 | Sluijter et al. |
| 5,654,279 A | 8/1997 | Rubinsky et al. |
| 5,665,382 A | 9/1997 | Grinstaff et al. |
| 5,674,218 A | 10/1997 | Rubinsky et al. |
| 5,709,855 A | 1/1998 | Bockow |
| 5,720,743 A | 2/1998 | Bischof et al. |

(Continued)

FOREIGN PATENT DOCUMENTS

SU   1266532 A   * 10/1986

OTHER PUBLICATIONS

Heish. Effects of ultrasound and diclofenac phonophoresis on inflammatory pain relief: suppression of inducible nitric oxide synthase in arthritic rats. Physical Therapy 2006; 86:39-49.

(Continued)

*Primary Examiner*—Roy D Gibson
*Assistant Examiner*—Kaitlyn E Helling

(57) ABSTRACT

The method and device of the present invention for pain relief using ultrasound waves in combination with cryogenic energy includes a generator and a transducer to produce ultrasonic waves and a cryogenic source to produce cryogenic energy. Ultrasound waves are delivered to the target in combination with cryogenic energy. Ultrasound waves and cryogenic energy can be delivered to the target from the radial side of the ultrasound horn and/or tip or can be delivered from the distal end of the ultrasound tip. Cryogenic energy can also be delivered directly to the target through a central orifice. Ultrasound energy can also be delivered through a cryogenic spray at the distal end. The use of ultrasound waves in combination with cryogenic energy can provide an analgesic effect.

7 Claims, 3 Drawing Sheets

U.S. PATENT DOCUMENTS

| | | |
|---|---|---|
| 5,733,280 A | 3/1998 | Avitall |
| 5,741,248 A | 4/1998 | Stern et al. |
| 5,755,755 A | 5/1998 | Panyard |
| 5,786,578 A | 7/1998 | Christy et al. |
| 5,820,626 A | 10/1998 | Baumgardner |
| 5,840,715 A | 11/1998 | Florio |
| 5,885,274 A | 3/1999 | Fullmer et al. |
| 5,906,612 A | 5/1999 | Chinn |
| 5,968,034 A | 10/1999 | Fullmer et al. |
| 5,976,092 A | 11/1999 | Chinn |
| 5,976,123 A | 11/1999 | Baumgardner et al. |
| 6,007,570 A | 12/1999 | Sharkey et al. |
| 6,011,022 A | 1/2000 | El Khoury |
| 6,030,374 A | 2/2000 | McDaniel |
| 6,048,337 A | 4/2000 | Svedman |
| 6,058,938 A | 5/2000 | Chu et al. |
| 6,063,108 A | 5/2000 | Salansky et al. |
| 6,068,628 A | 5/2000 | Fanton et al. |
| 6,073,051 A | 6/2000 | Sharkey et al. |
| 6,095,149 A | 8/2000 | Sharkey et al. |
| 6,126,682 A | 10/2000 | Sharkey et al. |
| 6,136,795 A | 10/2000 | Florio |
| 6,143,278 A | 11/2000 | Elkhoury |
| 6,168,593 B1 | 1/2001 | Sharkey et al. |
| 6,183,434 B1 | 2/2001 | Eppstein |
| 6,200,308 B1 | 3/2001 | Pope et al. |
| 6,210,393 B1 | 4/2001 | Brisken |
| 6,231,528 B1 | 5/2001 | Kaufman et al. |
| 6,245,347 B1 | 6/2001 | Zhang et al. |
| 6,261,311 B1 | 7/2001 | Sharkey et al. |
| 6,267,737 B1 | 7/2001 | Meilus |
| 6,303,142 B1 | 10/2001 | Zhang et al. |
| 6,306,431 B1 | 10/2001 | Zhang et al. |
| RE37,463 E | 12/2001 | Altman |
| 6,340,472 B1 | 1/2002 | Zhang et al. |
| 6,391,026 B1 | 5/2002 | Hung et al. |
| 6,398,753 B2 | 6/2002 | McDaniel |
| 6,402,739 B1 | 6/2002 | Neev |
| 6,410,599 B1 | 6/2002 | Johnson |
| 6,413,253 B1 | 7/2002 | Koop et al. |
| 6,414,032 B1 | 7/2002 | Johnson |
| 6,432,102 B2 | 8/2002 | Joye et al. |
| 6,436,078 B1 | 8/2002 | Svedman |
| 6,461,316 B1 | 10/2002 | Lee et al. |
| 6,465,006 B1 | 10/2002 | Zhang et al. |
| 6,478,754 B1 | 11/2002 | Babaev |
| 6,478,793 B1 | 11/2002 | Cosman et al. |
| 6,494,874 B1 | 12/2002 | Brisken |
| 6,494,900 B1 | 12/2002 | Salansky et al. |
| 6,503,243 B1 | 1/2003 | Brisken |
| 6,514,244 B2 | 2/2003 | Pope et al. |
| 6,517,536 B2 | 2/2003 | Hooven et al. |
| 6,517,568 B1 | 2/2003 | Sharkey et al. |
| 6,533,803 B2 | 3/2003 | Babaev |
| 6,544,401 B1 | 4/2003 | Colic |
| 6,546,935 B2 | 4/2003 | Hooven |
| 6,547,784 B1 | 4/2003 | Thompson et al. |
| 6,547,810 B1 | 4/2003 | Sharkey et al. |
| 6,562,033 B2 | 5/2003 | Shah et al. |
| 6,569,099 B1 | 5/2003 | Babaev |
| 6,601,581 B1 | 8/2003 | Babaev |
| 6,613,044 B2 | 9/2003 | Carl |
| 6,613,350 B1 | 9/2003 | Zhang et al. |
| 6,622,731 B2 | 9/2003 | Daniel et al. |
| 6,623,444 B2 | 9/2003 | Babaev |
| 6,638,276 B2 | 10/2003 | Sharkey et al. |
| 6,645,202 B1 | 11/2003 | Pless et al. |
| 6,645,203 B2 | 11/2003 | Sharkey et al. |
| 6,652,473 B2 | 11/2003 | Kaufman et al. |
| 6,652,864 B1 | 11/2003 | Webb et al. |
| 6,663,554 B2 | 12/2003 | Babaev |
| 6,663,622 B1 | 12/2003 | Foley et al. |
| 6,685,702 B2 | 2/2004 | Quijano et al. |
| 6,712,816 B2 | 3/2004 | Hung et al. |
| 6,723,064 B2 | 4/2004 | Babaev |
| 6,726,685 B2 | 4/2004 | To et al. |
| 6,733,496 B2 | 5/2004 | Sharkey et al. |
| 6,736,835 B2 | 5/2004 | Pellegrino et al. |
| 6,746,401 B2 | 6/2004 | Panescu |
| 6,749,605 B2 | 6/2004 | Ashley et al. |
| 6,752,805 B2 | 6/2004 | Maguire et al. |
| 6,756,053 B2 | 6/2004 | Zhang et al. |
| 6,759,434 B2 | 7/2004 | Johnson |
| 6,761,715 B2 | 7/2004 | Carroll |
| 6,761,729 B2 | 7/2004 | Babaev |
| 6,767,347 B2 | 7/2004 | Sharkey et al. |
| 6,780,426 B2 | 8/2004 | Zhang et al. |
| 6,787,149 B1 | 9/2004 | El Khoury et al. |
| 6,805,128 B1 | 10/2004 | Pless et al. |
| 6,805,129 B1 | 10/2004 | Pless et al. |
| 6,815,694 B2 | 11/2004 | Sfez et al. |
| 6,832,997 B2 | 12/2004 | Uchida et al. |
| 6,855,133 B2 | 2/2005 | Svedman |
| 6,868,286 B1 | 3/2005 | Hille et al. |
| 6,878,155 B2 | 4/2005 | Sharkey et al. |
| 6,881,214 B2 | 4/2005 | Cosman et al. |
| 6,887,861 B1 | 5/2005 | Hill et al. |
| 6,889,694 B2 | 5/2005 | Hooven |
| 6,896,673 B2 | 5/2005 | Hooven |
| 6,908,448 B2 | 6/2005 | Redding, Jr. |
| 6,923,806 B2 | 8/2005 | Hooven et al. |
| 6,932,811 B2 | 8/2005 | Hooven et al. |
| 6,937,893 B2 | 8/2005 | Danz et al. |
| 6,939,348 B2 | 9/2005 | Malecki et al. |
| 6,974,454 B2 | 12/2005 | Hooven |
| 6,984,233 B2 | 1/2006 | Hooven |
| 6,997,941 B2 | 2/2006 | Sharkey et al. |
| 7,001,415 B2 | 2/2006 | Hooven |
| 7,004,933 B2 | 2/2006 | McDaniel |
| 2001/0007940 A1 | 7/2001 | Tu et al. |
| 2001/0031961 A1 | 10/2001 | Hooven |
| 2002/0032440 A1 | 3/2002 | Hooven et al. |
| 2002/0091382 A1 | 7/2002 | Hooven |
| 2002/0091384 A1 | 7/2002 | Hooven et al. |
| 2002/0095144 A1 | 7/2002 | Carl |
| 2002/0103484 A1 | 8/2002 | Hooven |
| 2002/0107513 A1 | 8/2002 | Hooven |
| 2002/0107514 A1 | 8/2002 | Hooven |
| 2002/0115993 A1 | 8/2002 | Hooven |
| 2002/0120316 A1 | 8/2002 | Hooven et al. |
| 2002/0128639 A1 | 9/2002 | Pless et al. |
| 2002/0133148 A1 | 9/2002 | Daniel et al. |
| 2002/0133151 A1 | 9/2002 | Hung et al. |
| 2002/0143326 A1 | 10/2002 | Foley et al. |
| 2002/0161360 A1 | 10/2002 | Carroll |
| 2002/0165529 A1 | 11/2002 | Danek |
| 2003/0014098 A1 | 1/2003 | Quijano et al. |
| 2003/0032952 A1 | 2/2003 | Hooven |
| 2003/0093068 A1 | 5/2003 | Hooven |
| 2003/0122579 A1 | 7/2003 | Uzelac |
| 2003/0236560 A1* | 12/2003 | Babaev ........................ 607/50 |
| 2004/0059328 A1 | 3/2004 | Daniel et al. |
| 2004/0064152 A1 | 4/2004 | Zvuloni |
| 2004/0073203 A1 | 4/2004 | Yu et al. |
| 2004/0093042 A1 | 5/2004 | Altshuler et al. |
| 2004/0147912 A1 | 7/2004 | Sinofsky |
| 2004/0158237 A1 | 8/2004 | Abboud et al. |
| 2004/0162596 A1 | 8/2004 | Altshuler et al. |
| 2004/0167503 A1 | 8/2004 | Sinofsky |
| 2004/0215181 A1 | 10/2004 | Christopherson et al. |
| 2004/0215237 A1 | 10/2004 | Christopherson et al. |
| 2004/0215295 A1 | 10/2004 | Littrup et al. |
| 2004/0220648 A1 | 11/2004 | Carroll |
| 2004/0249372 A1 | 12/2004 | Capuano et al. |

| | | |
|---|---|---|
| 2005/0033274 A1 | 2/2005 | Pless et al. |
| 2005/0033282 A1 | 2/2005 | Hooven |
| 2005/0033283 A1 | 2/2005 | Hooven |
| 2005/0055053 A1 | 3/2005 | Phalen et al. |
| 2005/0149007 A1 | 7/2005 | Carl |
| 2005/0171530 A1 | 8/2005 | Hooven |
| 2005/0182393 A1 | 8/2005 | Abboud et al. |
| 2005/0192565 A1 | 9/2005 | Eum et al. |
| 2005/0203505 A1 | 9/2005 | Megerman et al. |
| 2005/0222649 A1 | 10/2005 | Capuano et al. |
| 2005/0224086 A1 | 10/2005 | Nahon |
| 2005/0251125 A1 | 11/2005 | Pless et al. |

OTHER PUBLICATIONS

Young & Dyson. Effects of therapeutic ultrasound on the healing of full-thickness excised skin lesions. Ultrasonics 1990; 28: 175-180.

Dino et al. The significance of membrane changes in safe and effective use of therapeutic and diagnostic ultrasound. Physics in Medicine and Biology, 1989; 34: 1543-1552.

Constantino et al., "Cryoultrasound therapy and tendonitis in athletes." Act Bio Med, April 200; 76; 37-41.

Medisport, "CryoUltrasound", Mar. 28, 2006—Retrieved from www.medisport.it—please note that the second half of the document is an English translation of the first half of the document.

* cited by examiner

APPARATUS AND METHODS FOR PAIN RELIEF USING ULTRASOUND WAVES IN COMBINATION WITH CRYOGENIC ENERGY

BACKGROUND OF THE INVENTION

1. Field of the Invention

The present invention relates to pain relief. In particular, the present invention relates to apparatus and methods for pain relief using ultrasound waves in combination with cryogenic energy.

2. Description of the Related Art

The use of ultrasound as a source of heat to treat pain is well known in the art. Heat generated by ultrasound is utilized to treat pain by either ablating the nociceptive nerve and nerve endings responding to the pain (for example U.S. Pat. No. 5,433,739 to Sluijter et al and U.S. Pat. No. 6,073,051 to Sharkey et al) or by warming the target tissue (for example U.S. Pat. No. 5,460,595 to Hall et al and U.S. Pat. No. 5,413,550 to Castel). The former method treats pain by permanently removing the body's ability to sense pain in the treated area. It has been suggested that damage to tissue surrounding the target tissue to be ablated by ultrasonic energy can be reduced by cooling the ultrasound electrode (U.S. Pat. No. 5,186,181 to Franconi et al). While removing the ability to sense to pain may provide short-term therapeutic benefits, it can cause long term harm by preventing the patient from detecting the development of new pathologies or the worsening of existing pathologies in the treated area. Unable to sense the pain associated with pathologic changes, the patient will delay seeking treatment thereby lowering the patient's prognosis.

Treating pain by heating the target tissue with ultrasonic energy has been proven effective. Assuming the therapeutic effects of ultrasound administration are tied to a thermal effect, these methods attempt to raise the temperature of the target tissue anywhere from 1 to 4 degree Celsius; deep pain and chronic pain are treated with higher temperatures (U.S. Pat. No. 5,413,550 to Castel). Heating target tissue, however, runs the risk of burning the patient or otherwise producing patient discomfort. Furthermore, studies investigating the therapeutic effects of ultrasound suggest that analgesic effects are not dependent upon the thermal effects of ultrasound. (Hsieh. Effects of ultrasound and diclofenac phonophoresis on inflammatory pain relief: suppression of inducible nitric oxide synthase in arthritic rats. *Physical Therapy* 2006; 86: 39-49; Young and Dyson. Effect of therapeutic ultrasound on the healing of full-thickness excised skin lesions. *Ultrasonics* 1990; 28: 175-180; Dino et al. The significance of membrane changes in the safe and effective use of therapeutic and diagnostic ultrasound. *Physics in Medicine and Biology* 1989; 34: 1543-1552.) Thus the use of ultrasound as an analgesic heat source is misguided and exposes the patient to unnecessary risks.

The use of cold temperatures to provide pain relief is also well-known. The most frequent use is the standard ice-pack that is used in everyday homes. The analgesic effect cool temperature provides stems from the cooling of neuronal tissue that causes the neuronal tissue to cease functioning. The use of cold temperatures for pain relief has evolved into a different format: cryogenics are now used to cool or freeze neuronal tissue such as nerves to produce an analgesic effect. The freezing of the tissue, however, provides a more dramatic effect than the simple cooling of neuronal tissue. Nerves are destroyed because the freezing of nerve cell bodies kills the cell body. For example, U.S. Pat. No. 6,761,715 to Carroll discloses a system and method for cooling or freezing neuronal tissue in order to induce lesions and produce cryoanalgesia. Additionally, U.S. Pat. No. 5,571,147 to Sluijter et al. discloses a general method of denervation of nerves to relieve back pain using both heating and cryogenic methods. While these methods may result in an analgesic effect, the drawback of these methods is that they result in the destruction of nerves. The present invention does not involve the destruction of tissues, cell, or nerves through heating, freezing, etc to provide pain relief.

U.S. Pat. Application No. 2002/0165529 to Danek discloses a system and method that utilizes cryogenic energy in combination with other sources of energy such as ultrasound or microwave to prevent collateral damage to the surface layer because of the high temperatures used. U.S. Pat. Application No. 2003/0014098 to Quijano et al. also uses cryogenic energy to protect peripheral tissue from applied thermal energy. The present invention does not us cryogenic energy to prevent collateral damage; the cryogenic energy used in the present invention is for an additional therapeutic purpose for pain relief.

Therefore, there is a need for a method and device that utilize both ultrasound energy and cryogenic energy in combination to provide effective pain relief that does not result in destruction of tissues, cells, or nerves.

SUMMARY OF THE INVENTION

The present invention is directed towards an apparatus and methods for pain relief using ultrasound waves in combination with cryogenic energy. Apparatus and methods in accordance with the present invention may meet the above-mentioned needs and also provide additional advantages and improvements that will be recognized by those skilled in the art upon review of the present disclosure.

The present invention comprises an ultrasonic generator powering an ultrasonic transducer connected to the proximal end of a sonotrode with an internal chamber. A cryogenic fluid from a cryogenic fluid supply source is circulated through the internal chamber of the sonotrode. Utilizing ultrasonic waves in combination with cryogenic energy provides more effective pain relief than when either is used alone.

Ultrasonic energy is delivered directly to the area of the body to be treated for pain by contacting the area with the radial side of the sonotrode (the combination of ultrasound horn and tip). Ultrasound energy provides a pain relief effect because it positively influences nerve endings, massages tissues, and stimulates cells.

Cryogenic energy is delivered in combination with ultrasound energy. Cryogenic fluids, such as cryogenic liquids or gases, can be circulated through the sonotrode, thus causing the temperature of the sonotrode to decrease. The use of cryogenic energy also provides a cooling effect on the area of the body to be treated for pain when delivered by either contacting a cooled sonotrode to the area of the body or by spraying a cryogenic fluid onto the area through an orifice in the ultrasound tip. The use of cryogenic energy can provide pain relief itself.

It should be noted that, unlike other cryogenic treatment methods, the cooling effect with the cryogenic energy according to the present invention is not meant to freeze or destroy any tissues, cells, nerve endings, etc. Accordingly, the flow of cryogenic fluid through the chamber of the sonotrode should cool the portion of the pain relief apparatus contacting the body to a temperature that does not freeze or destroy tissue. Likewise, the cryogenic fluid sprayed onto the body from the tip should cool the sprayed area of the body to a temperature that does not freeze or destroy tissue. The use of concurrent cryogenic pain relief can also increase the effectiveness of the ultrasound pain relief.

BRIEF DESCRIPTION OF THE DRAWINGS

The present invention will be shown and described with reference to the drawings of preferred embodiments and clearly understood in detail. Like elements of the various embodiments depicted within the figures are equivalently numbered.

DETAILED DESCRIPTION OF THE INVENTION

The present invention is an apparatus and methods for pain relief using ultrasound waves in combination with cryogenic energy. Preferred embodiments of the present invention in the context of an apparatus and methods are illustrated in the figures and described in detail below.

Figure 1:
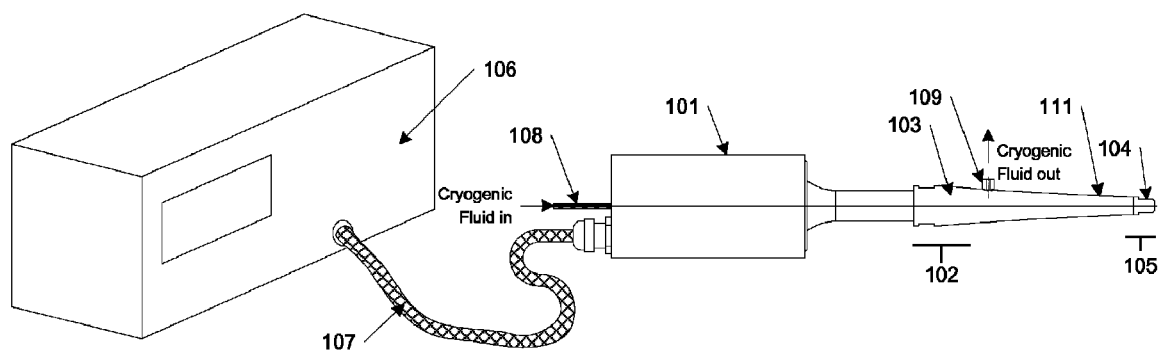
FIG. 1 is a perspective view of an ultrasound and cryogenic pain relief apparatus for use according to the present invention.

FIG. 1 illustrates an embodiment of an ultrasound and cryogenic pain relief apparatus comprising an ultrasonic transducer 101 connected to the proximal end 102 of a sonotrode comprising an ultrasonic horn 103 and an ultrasonic tip 104 at the distal end 105 of the sonotrode. During operation, power received from generator 106 via power cord 107 drives transducer 101. Cryogenic fluid received by feed port 108 and vented from exit port 109 on radial surface 111 is circulated through tip 104. Flowing into and out of sonotrode the cryogenic fluid cools at a portion of the sonotrode to a temperature that does not freeze or destroy tissue. One example of a cryogenic fluid to use is liquid nitrogen; other cryogenic liquids and/or gases may also be effective.

Figure 2:
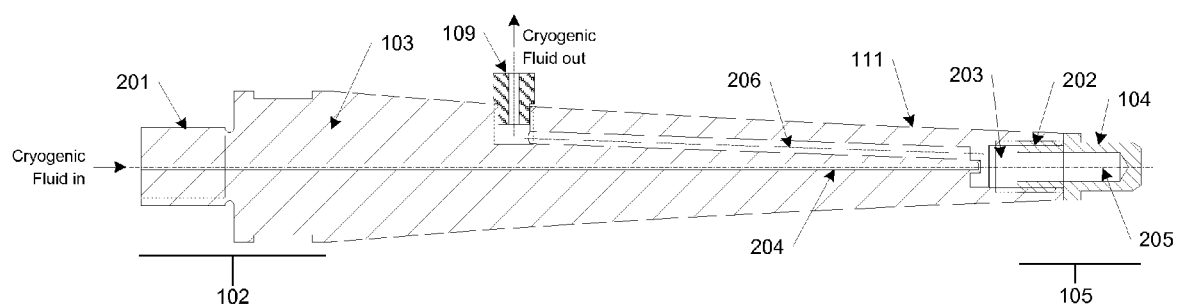
FIG. 2 is a cross-sectional view of an ultrasound and cryogenic pain relief apparatus.

FIG. 2 illustrates a cross-sectional view of the sonotrode of the ultrasound and cryogenic pain relief apparatus shown in FIG. 1. Ultrasonic transducer 101 is mechanically connected to the ultrasound horn 103 by a threaded protrusion 201 on the proximal end of horn 103. Alternatively, the ultrasonic transducer 101 may be directly connected to the ultrasound horn 103 to comprise a single piece without a mechanical interface. The ultrasound horn 103 is also mechanically connected to the ultrasound tip 104. In the embodiment depicted, tip 104 contains a threaded portion 202 at its proximal end that is received by a threaded recess 203 in the distal end of horn 103. Alternatively, the ultrasound tip 104 could be directly connected to the ultrasound horn 103 to comprise a single piece without a mechanical interface.

Though the ultrasound tip 104 depicted in FIGS. 1 and 2 contains a rounded edge encircling a flat distal end surface, the tip 104 could comprise a curved and/or spherical distal end surface. Likewise, the edge surrounding the distal end surface of tip 104 could be blunt and/or tapered. Furthermore, the distal end radiation surface can be formed in any shape and thus need not be circular, as depicted in FIGS. 1 and 2.

Cryogenic fluid is inserted into the cryogenic fluid entry port 108. The cryogenic fluid then moves through the entry channel 204 and into chamber 205 within tip 104. The cryogenic fluid then exits chamber 205 through the exit channel 206. The cryogenic fluid then exits horn 103 through the exit port 109 that is inserted into the proximal end of exit channel 206 in radial surface 111 of the sonotrode's ultrasound horn 103. The flow of cryogenic fluid through the tip and horn cools at least a portion of the tip and/or horn to a temperature that does not freeze or destroy tissue. Thus, channels 204 and 206 permit a flow of cryogenic fluid into and out of chamber 205 that cools at least a portion of the apparatus to a temperature that does not freeze or destroy tissue. A tube or other material can replace the entry channel 204 and the exit channel 206.

Figure 3:
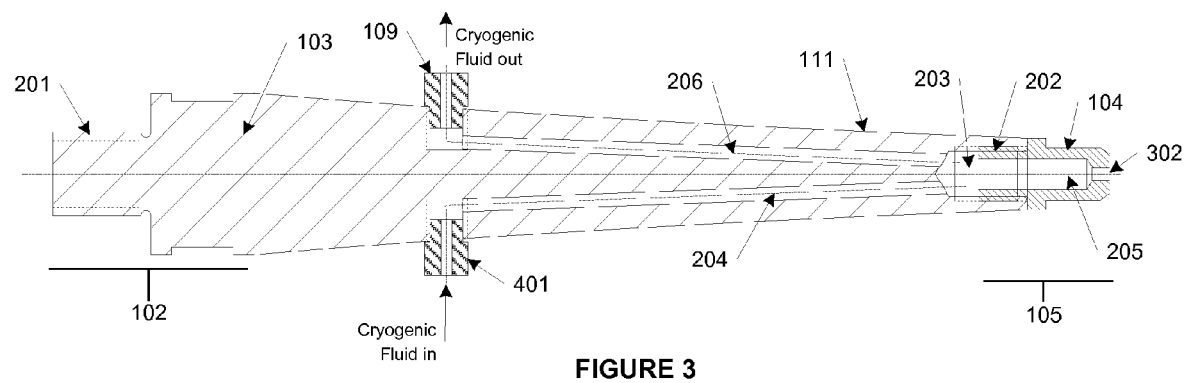
FIG. 3 is a detailed cross-sectional view of an ultrasound horn and tip combination lacking an orifice within the tip.

FIG. 3 is a detailed cross-sectional view of the sonotrode section of an ultrasound and cryogenic pain relief apparatus in which cryogenic entry channel 204 and exit channel 206 have proximal ends opening into surface 111 of the sonotrode's ultrasound horn 103. When both channels 204 and 206 have their proximal ends within a radial surface of horn 103, it is preferred that their proximal ends are located on directly opposite sides of the ultrasound horn 103. Entry ports 109 and 301, if included, should be orientated ninety-degrees to the axis of the sonotrode, though they may be orientated at any other angle to the axis-of the sonotrode. The proximal ends of channels 206 and/or 204 may be located off-center in the ultrasound horn 103.

The embodiment depicted in FIG. 3 further comprises orifice 302 within tip 104. The inclusion of orifice 302 permits at least a portion of the cryogenic fluid circulating through the chamber 205 to be sprayed onto the area to be treated for pain, as to cool the area to a temperature that does not freeze or destroy tissue.

In addition or in the alternative to cooling an area of the body, a spray of cryogenic fluid may act as a conduit for the transmission of ultrasound energy emanating from the apparatus. Acting as a conduit, a spray of cryogenic fluid may enable the delivery of ultrasonic energy to an area of the body without contacting the area directly with the apparatus. Therefore, an indirect delivery of ultrasound energy may be accomplished with a cryogenic spray.

The frequency range for the ultrasound vibrations induced in the sonotrode by the transducer is 15 kHz to 40 MHz, with a preferred frequency range of 20 kHz-60 kHz, and the recommended frequency value is 30 kHz. The amplitude of the ultrasound vibrations induced in the sonotrode by the transducer can be 1 micron and above, with a preferred amplitude range of 10 microns to 250 microns, and with a most preferred amplitude range of 20 microns to 70 microns, and the recommended amplitude value is 50 microns. Inducing vibrations can be accomplished by driving the transducer with a continuous, pulsed, fixed and/or modulated frequency. The driving wave of the transducer inducing vibrations in the horn and tip may be a sinusoidal, rectangular trapezoidal, and/or triangular wave form. The time of treatment and the number of treatments will vary based on a variety of factors. These factors include the type of pain being treated (chronic, acute, phantom, etc), the source of the pain (cut, bruise, burn, etc), the periodicity of the symptoms, the duration of the pain, the reaction of the patient to the treatment, etc.

Ultrasonic waves are delivered in combination with cryogenic energy to provide more effective pain relief. Ultrasound waves and cryogenic energy can be delivered either concurrently or sequentially. Radial ultrasound waves can be delivered by directly contacting the radial sides of the sonotrode to the area of the body to be treated for pain. Cryogenic energy can be delivered by directly contacting the cooled sonotrode to the area of the body to be treated for pain. The preferred method of treatment is to deliver radial ultrasound waves from the radial side of the sonotrode and to also deliver cryogenic energy from the radial side of the sonotrode. Ultrasound waves delivered alone from the radial side of the sonotrode can also provide pain relief. If the tip includes an orifice, delivering cryogenic energy may be accomplished by spraying the area of the body to be treated for pain with the cryogenic fluid. The spray of cryogenic fluid emanating from the tip may also act as a conduit for ultrasonic energy emanating from the tip. Using a cryogenic spray as a conduit allows for the indirect delivery of ultrasonic energy to the area of the body to be treated for pain.

Although specific embodiments and methods of use have been illustrated and described herein, it will be appreciated by those of ordinary skill in the art that any arrangement that is calculated to achieve the same purpose may be substituted for the specific embodiments and methods shown. It is to be understood that the above description is intended to be illustrative and not restrictive. Combinations of the above embodiments and other embodiments as well as combinations of the above methods of use and other methods of use will be apparent to those having skill in the art upon review of the present disclosure. The scope of the present invention should be determined with reference to the appended claims, along with the full scope of equivalents to which such claims are entitled.

I claim:

1. A method for pain relief by using ultrasound waves in combination with cryogenic energy, comprising the steps of:
    a. delivering radial ultrasonic waves having a frequency between 15 kHz and 40 MHz and an amplitude between 10 and 250 microns to an area of the body to be treated for pain; and
    b. cooling the area of the body to a temperature that does not destroy tissue.

2. The method according to claim 1, wherein the delivery of the radial ultrasound waves and the cooling of the area of the body to be treated for pain are done sequentially.

3. An apparatus for pain relief by using ultrasound waves in combination with cryogenic energy, comprising:
    a. a sonotrode containing:
        i. a proximal end;
        ii. a distal end opposite the proximal end; and
        iii. a radial surface extending between the distal end and the proximal end;
    b. a generator connected to a transducer attached to the proximal end of the sonotrode capable of inducing the sonotrode to vibrate at a frequency between 15 kHz and 40 MHz with an amplitude between 10 and 250 microns;
    c. at least two channels extending at least partially through the sonotrode and opening into a chamber within the sonotrode capable of permitting a flow of cryogenic fluid into and out of the chamber, wherein the flow of cryogenic fluid cools a portion of the radial surface of the sonotrode to a temperature that does not destroy tissue; and
    d. a cryogenic fluid source connected to at least on of the channels within the sonotrode.

4. The apparatus according to claim 3, wherein the generator drives the transducer with a continuous or pulsed frequency.

5. The apparatus according to claim 3, wherein the generator drives the transducer with a fixed or modulated frequency.

6. The apparatus according to claim 3, wherein the driving wave form of the transducer is selected from the group consisting of sinusoidal, rectangular, trapezoidal and triangular wave forms.

7. The method according to claim 1, wherein the delivery of the radial ultrasound waves and the cooling of the area of the body to be treated for pain are done simultaneously.

* * * * *